US00PP32192P3

(12) United States Plant Patent
Tufaro

(10) Patent No.: US PP32,192 P3
(45) Date of Patent: Sep. 15, 2020

(54) STRAWBERRY PLANT NAMED 'NSG 120'

(50) Latin Name: ***Fragaria* x *ananassa* Duchesne**
Varietal Denomination: NSG 120

(71) Applicant: Nova Siri Genetics S.r.l., Nova Siri (MT) (IT)

(72) Inventor: Nicola Tufaro, Nova Siri (IT)

(73) Assignee: NOVA SIRI GENETICS S.R.L., Nova Siri (MT) (IT)

( * ) Notice: Subject to any disclaimer, the term of this patent is extended or adjusted under 35 U.S.C. 154(b) by 0 days.

(21) Appl. No.: 16/501,377

(22) Filed: Apr. 3, 2019

(65) Prior Publication Data

US 2019/0327867 P1 Oct. 24, 2019

(30) Foreign Application Priority Data

Apr. 23, 2018 (QZ) ..... PBR 2018/1111

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./156, 208
See application file for complete search history.

(56) References Cited

U.S. PATENT DOCUMENTS

PP28,081 P3 6/2017 Tufaro
PP28,220 P3 7/2017 Tufaro

*Primary Examiner* — Susan McCormick Ewoldt
*Assistant Examiner* — Karen M Redden
(74) *Attorney, Agent, or Firm* — Buchanan Ingersoll & Rooney P.C.

(57) ABSTRACT

A new and distinct variety of strawberry plant, referred to by its cultivar name, 'NSG 120', is provided which forms in abundance attractive early-ripening large, medium red primarily conical fruit having firm flesh that is longer than broad in configuration. The growth habit is semi-dense, semi-upright. White inflorescence is displayed. Commonly a calyx is displayed which is larger than the diameter of the corolla when open. The new variety is particularly well suited for the commercial industry.

15 Drawing Sheets

Figure 1:
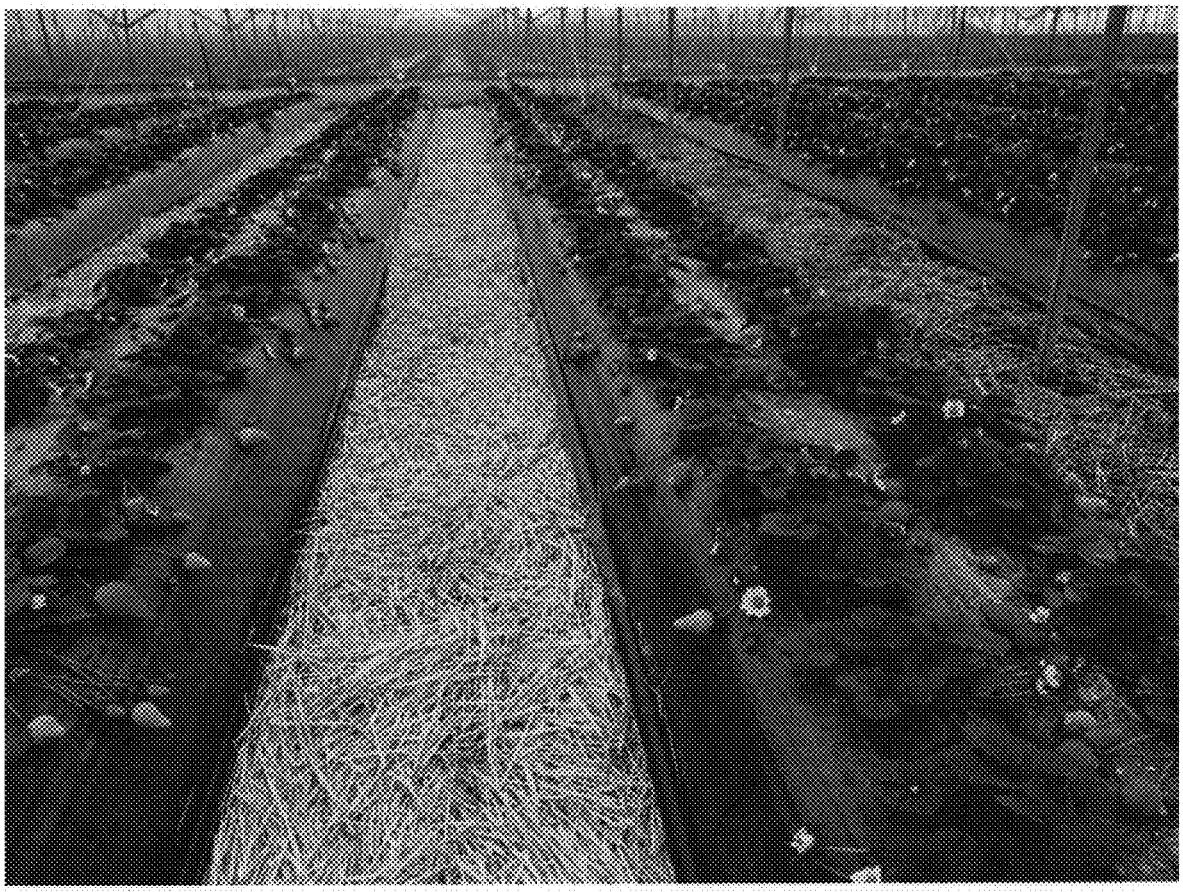

Botanical/commercial classification:
Latin name—*Fragaria* x *ananassa* Duchesne.
Varietal denomination: 'NSG 120'.

CROSS-REFERENCE TO RELATED APPLICATIONS

This application claims priority to Community Plant Variety Rights Application Number 2018/1111 which was filed in European Union through Community Plant Variety Office on Apr. 23, 2018, of which the content of is hereby expressly incorporated by reference in its entirety for all purposes.

SUMMARY OF THE INVENTION

The new and distinct short-day strawberry plant variety of the present invention was the product of a controlled breeding program that was carried out at Nova Siri (MT) Italy located at 40° 08' 40" N-16° 39' 40" E and 10 meters above sea level, wherein two parents were crossed which previously had been studied in the hope that they would contribute the desired characteristics. The female parent (i.e., the seed parent) was the CHARLENE variety (U.S. Plant Pat. No. 28,220 P3 and European Union Community Plant Variety Rights No. 45319), which is a strawberry variety plant with medium-season yield and produces fruit with high contents of sugar. The male parent (i.e., pollen parent) was the MELISSA variety (U.S. Plant Pat. No. 28,081 P3 and European Union Community Plant Variety Rights No. 45318), which is a strawberry variety with high early-season yield, produces very high yield and very large primary and secondary fruits.

The parentage can be summarized as follows:

'CHARLENE' x 'MELISSA'.

The seeds resulting from the above pollination were sown and small plants were obtained which were physically different from each other. Selective study and testing resulted in the identification of a single short-day strawberry plant of the new variety.

It was found that the new strawberry plant of the present invention possesses the following combination of characteristics:

(a) exhibits a semi-dense, semi-upright growth habit,
(b) displays, on an early basis, white inflorescence at a level generally above the foliage,
(c) commonly displays a calyx that is larger than the diameter of the corolla when open, and
(d) forms in abundance attractive early-ripening large, medium red primarily conical fruit having firm flesh that is longer than broad in configuration.

The new variety well meets the needs of the horticultural industry. The new variety possesses characteristics that commonly are sought by commercial strawberry growers. For example, the new variety provides uniform attractive firm medium red early-ripening fruit in good yields. Accordingly, the new variety is to be freshly consumed and is considered promising for commercial introduction. The new variety requires an induction period for flowering. This may be achieved by growing in a colder climate away from the equator or at a higher altitude above sea level.

The new variety can be readily distinguished from its ancestors. More specifically, the 'CHARLENE' variety (i.e., the seed parent) displays generally conical shape fruit which is darker in external and internal color compared to the conical, slightly rhomboid, shaped fruit of the new variety. Specifically, 'CHARLENE' displays fruit with an external color commonly near Red Group 45B to Red Group 46A and an internal color commonly near Orange-Red Group 34A to Orange-Red Group 34B, whereas the new variety displays fruit with an external color commonly near Red Group 43A to Red Group 43B and an internal color commonly near Orange-Red Group 33A to Orange-Red Group 33B. Additionally, the 'MELISSA' variety (i.e., the pollen parent) provides generally rhomboid shape fruit with an external color and internal core color which is darker compared to the conical, slightly rhomboid, shape fruit of the new variety. Specially, 'MELISSA' provides fruit with an external color commonly near Red Group 45B to Red Group 46B and an internal color commonly near Orange-Red Group 34A to Orange-Red Group 34B, whereas the new variety displays fruit with an external color commonly near Red Group 43A to Red Group 43B and an internal color commonly near Orange-Red Group 33A to Orange-Red Group 33B. Moreover, the new variety can be readily distinguished from non-parental related similar varieties. For example, the 'NSG 1117' variety (European Union Community Plant Variety Rights Application No. 2016/1694 and not patented in the U.S.) provides fruit that is darker in color compared to the fruit of the new variety and the time between first blooming and first fruit ripening for the 'NSG 1117' variety is longer compared to the new variety. Specifically, 'NSG 1117' provides fruit with an external color commonly near Red Group 45A and an internal color commonly near Red Group 42A, whereas the new variety is provides fruit with an external color commonly near Red Group 43A to Red Group 43B and an internal color commonly near Orange-Red Group 33A to Orange Red Group 33B.

The new variety has been found to undergo asexual propagation in Poland and Italy by a number of routes, including by use of stolons and in vitro tissue culture. Specifically, the new variety has been asexually reproduced in a nursery setting by the use of stolons at Zielona Gora-Ochla, Poland located at 51° 848 N-15° 447 E and at Nova Siri (MT), Italy by in vitro tissue culture. No rotting problems were observed on the roots during cultivation. The combination of characteristics exhibited by the new variety has been found to be stable and reliably transmitted to succeeding generations following such asexual reproduction. Accordingly, the new variety undergoes asexual propagation in a true-to-type manner by such asexual reproduction.

The new variety has been named 'NSG 120'. The new plant variety initially was designated as EE 14 P3 15 120.

BRIEF DESCRIPTION OF THE PHOTOGRAPHS

The accompanying photographs show, as nearly true as it is reasonably possible to make the same in color illustrations of this character, typical specimens of the new variety. The illustrated strawberry plants of the new variety were asexually reproduced by stolons in a nursery at Zielona Gora-Ochla, Poland at 51° 848 N-15° 447 E and were planted under the cover of plastic tunnels during mid-October 2017 at Nova Siri (MT), Italy located at 40° 08' 40" N-16° 39' 40" E at 10 meters above sea level.

FIG. 1—illustrates rows of early fruiting plants on Jan. 18, 2018, wherein the newly formed flowers are commonly disposed above the foliage and first early conical large red fruits are present.

Figure 2:
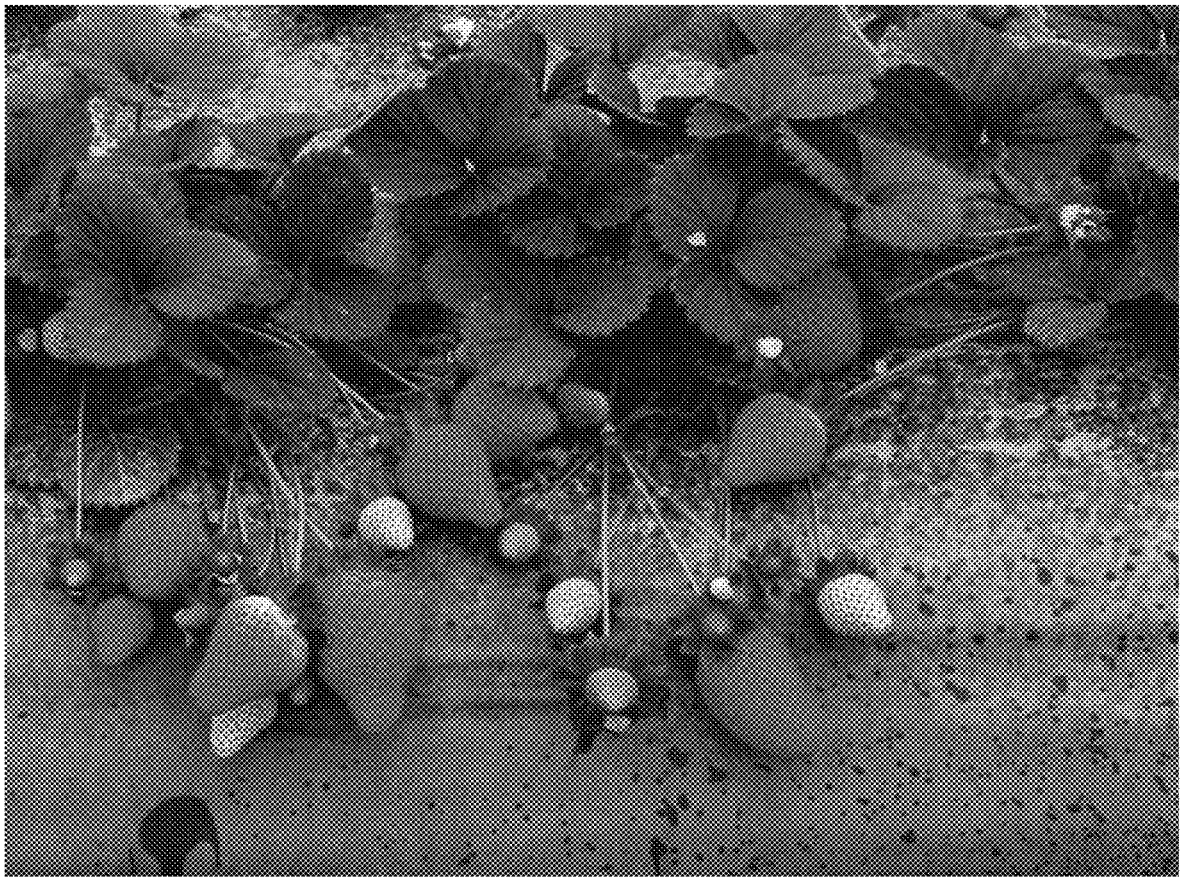

FIG. 2—illustrates two semi-upright fruiting plants on Feb. 8, 2018, wherein abundant early red fruit production is apparent.

Figure 3:
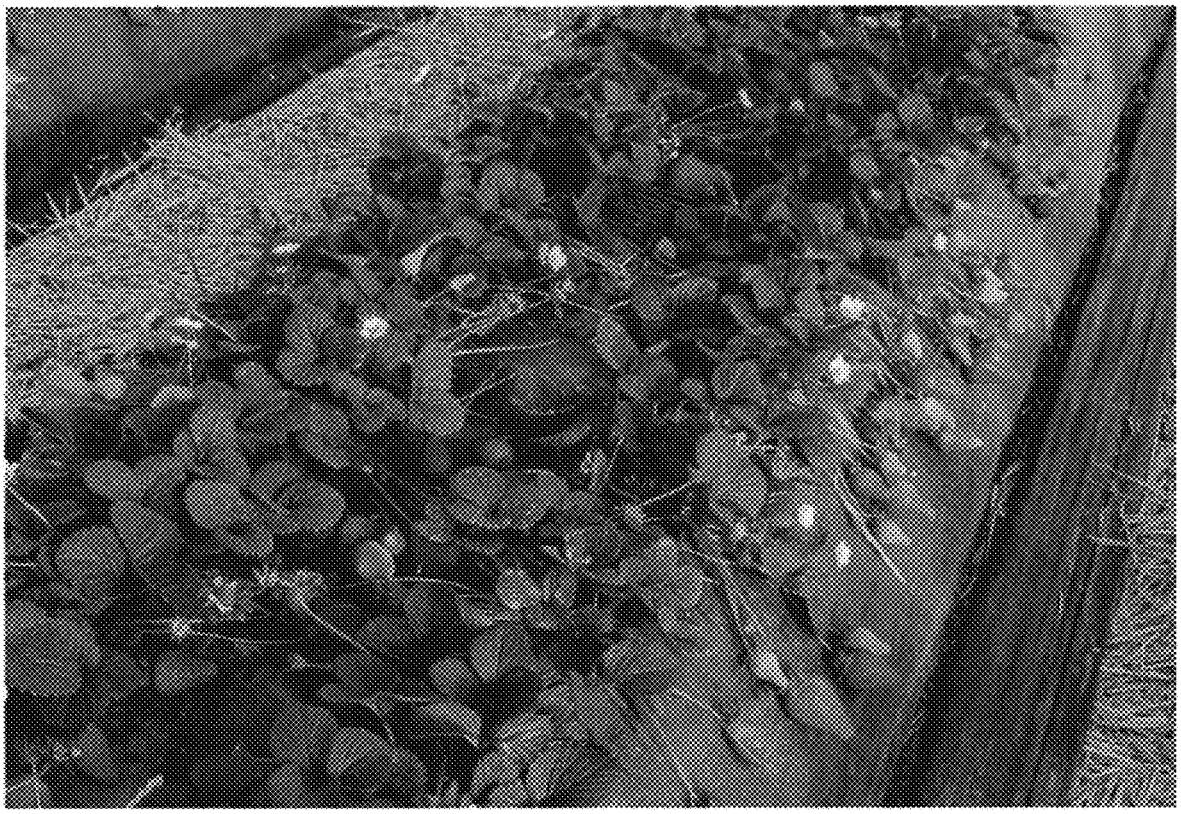

FIG. 3—illustrates a row of fruiting plants on Mar. 15, 2018, wherein medium vigor plants with semi-upright and semi-dense vegetation, newly formed flowers, uniform red fruits, and long peduncles are apparent.

Figure 4:
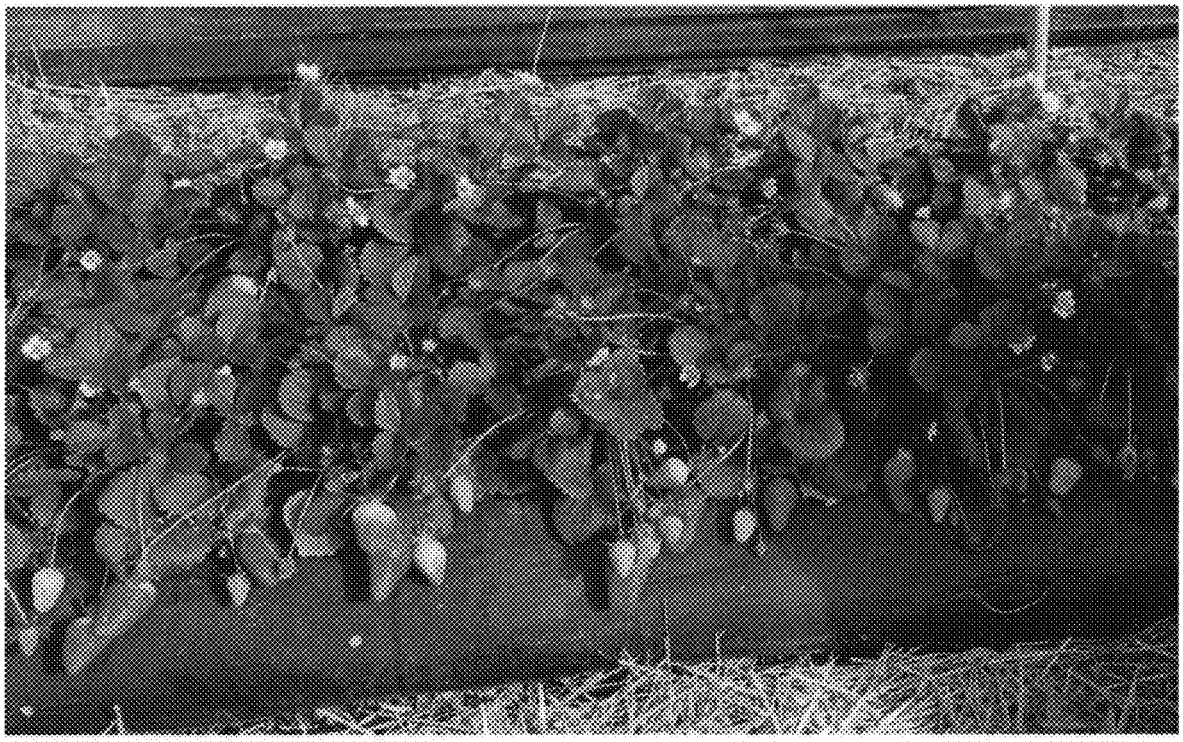

FIG. 4—illustrates a row of fruiting plants on Apr. 20, 2018, wherein abundant flowers and fruits in all phases of development are present.

Figure 5:
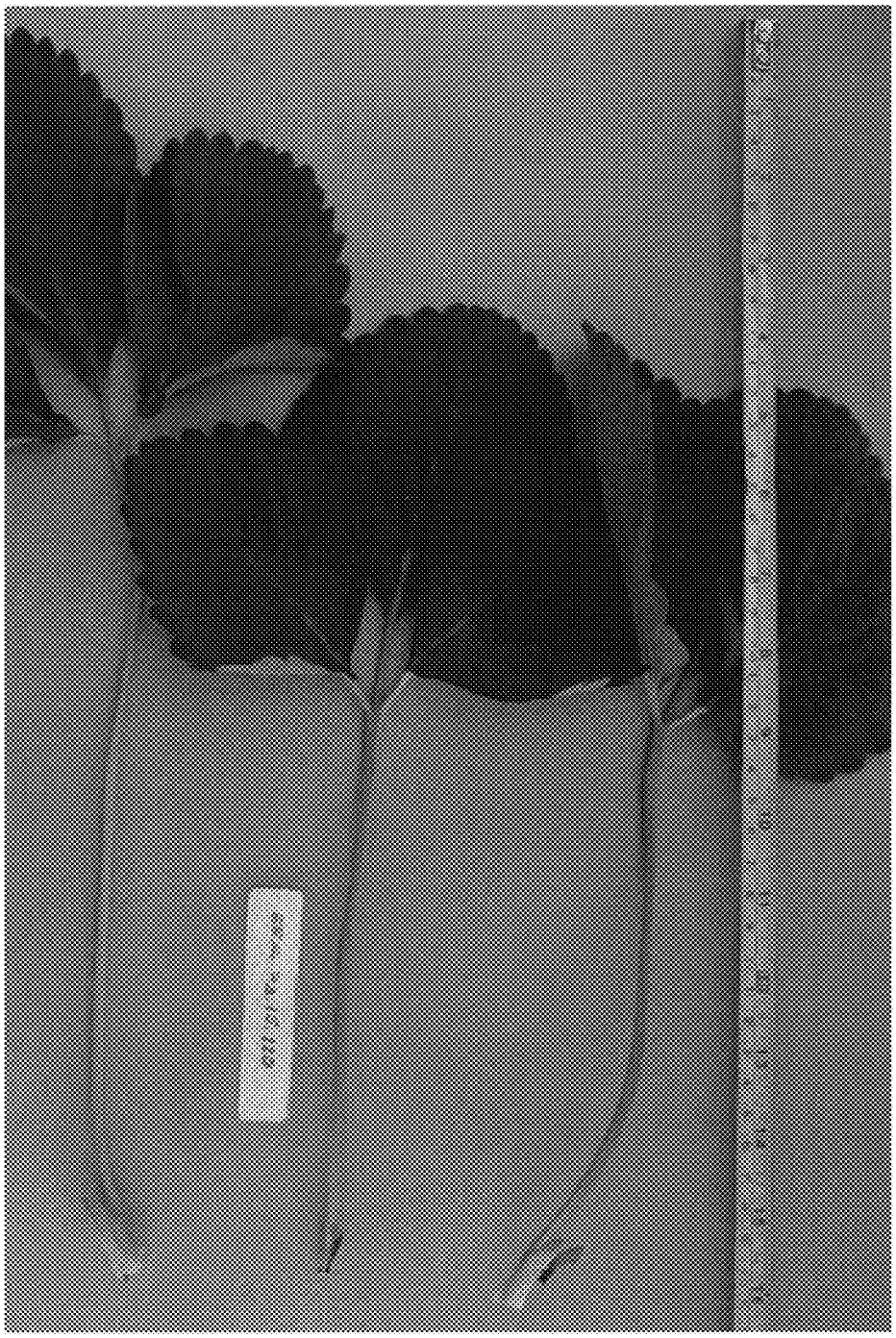

FIG. 5—illustrates specimens of three-leaflet leaves—upper surface, wherein the petiole and stipules are further apparent (designate in image as EE14.P3.15.120). Dimensions in centimeters and inches are included.

Figure 6:
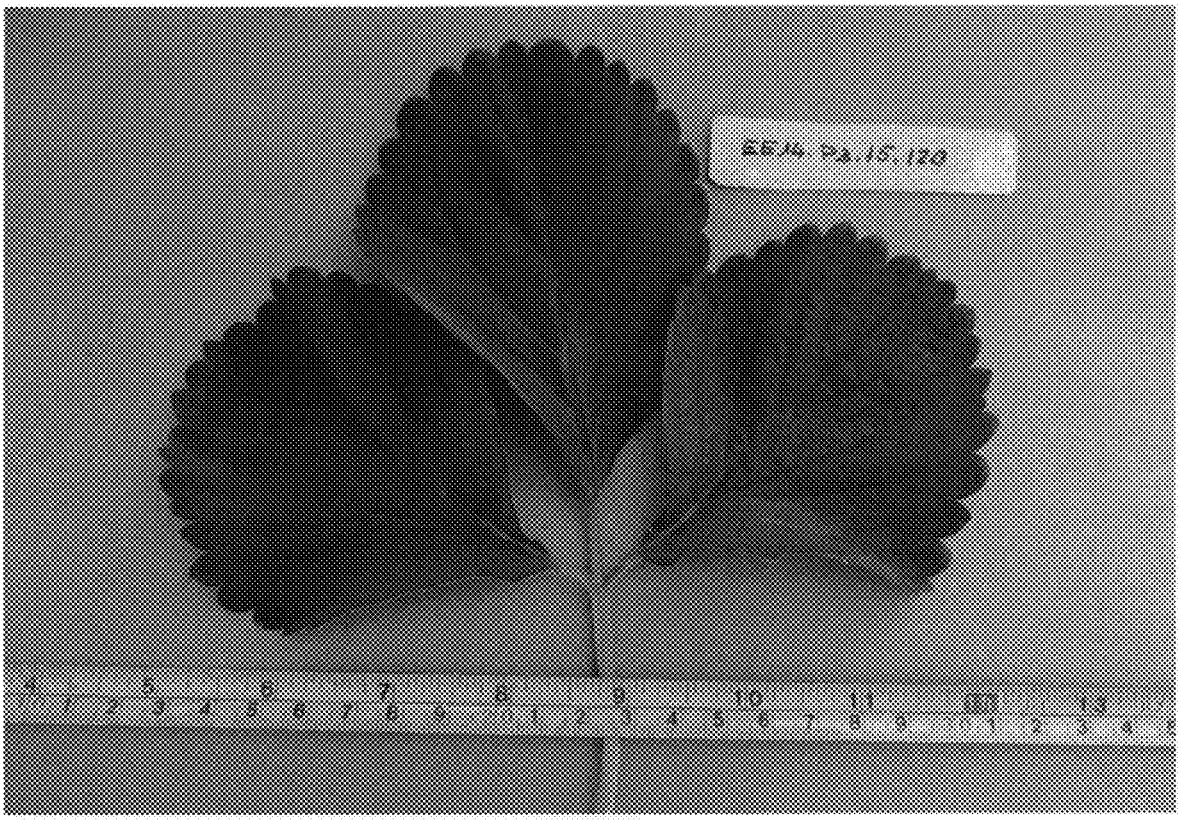

FIG. 6—illustrates a specimen of a typical three-leaflet leaf—upper surface (designate in image as EE14.P3.15.120). Dimensions in centimeters and inches are included.

Figure 7:
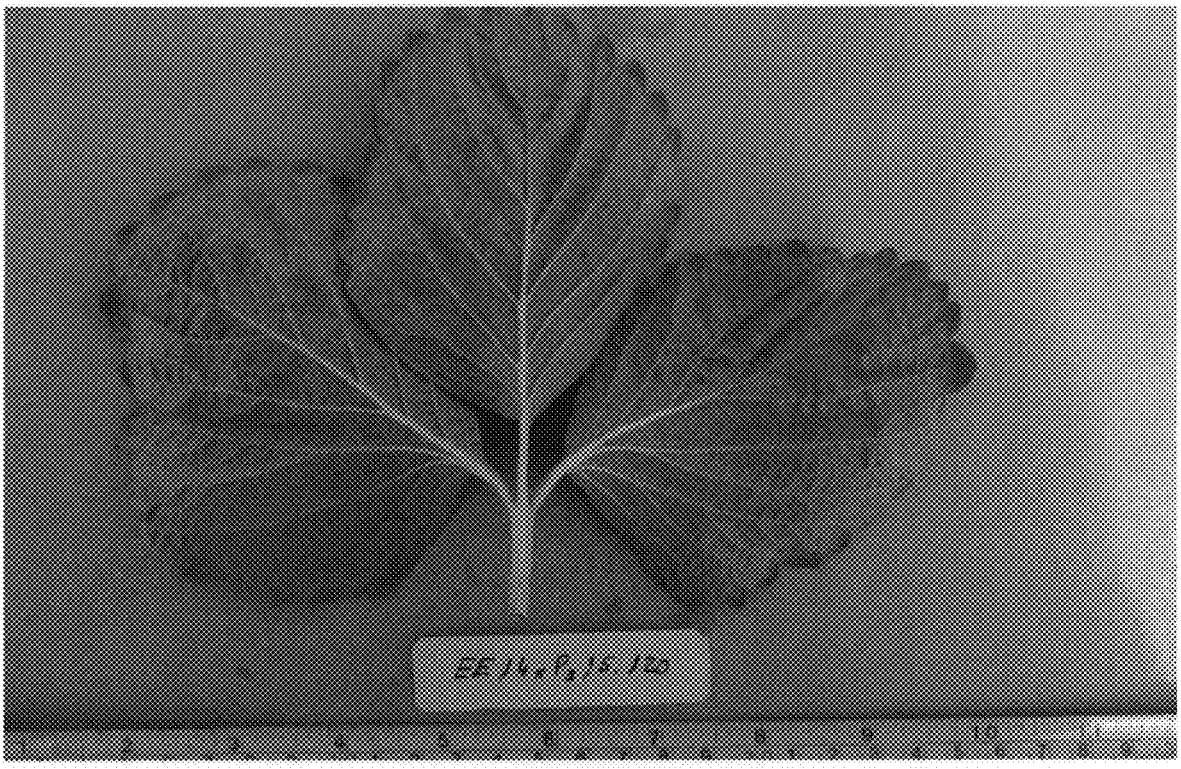

FIG. 7—illustrates a specimen of a typical three-leaflet leaf—under surface (designate in image as EE14.P3.15.120). Dimensions in centimeters and inches are included.

Figure 8:
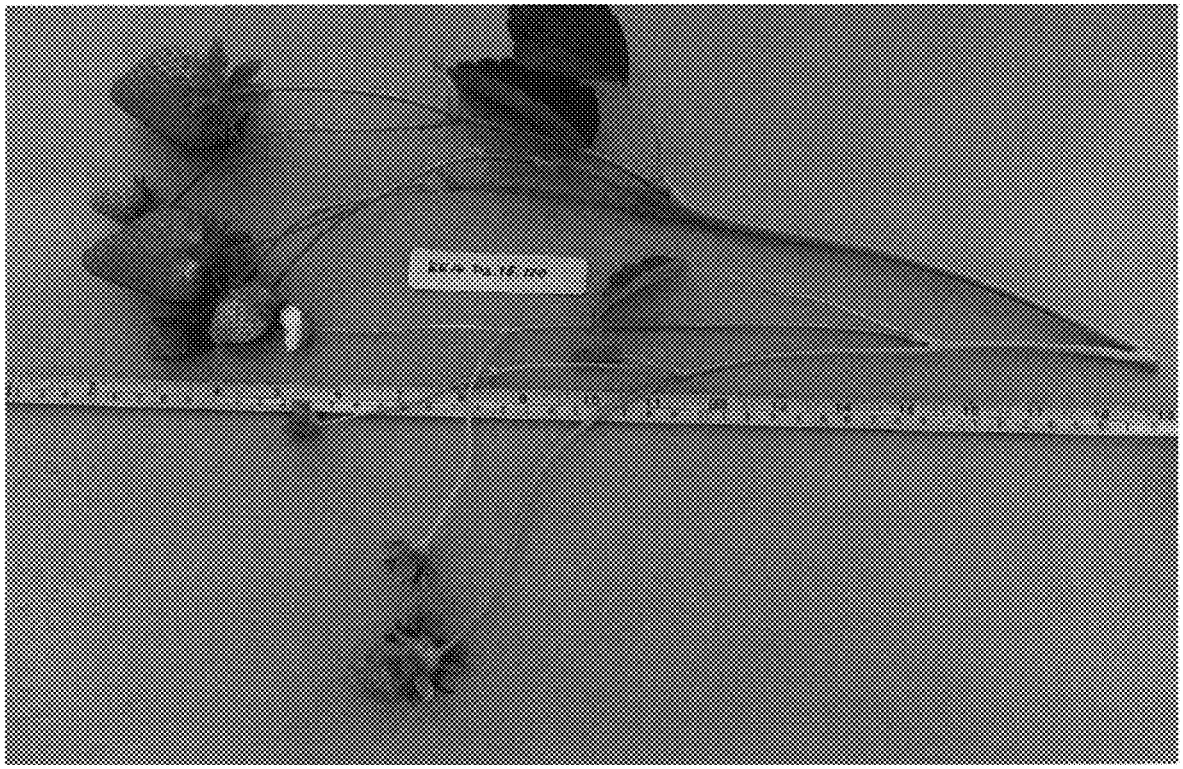

FIG. 8—illustrates a fruiting specimen (designate in image as EE14.P3.15.120). Dimensions in centimeters and inches are included.

Figure 9:
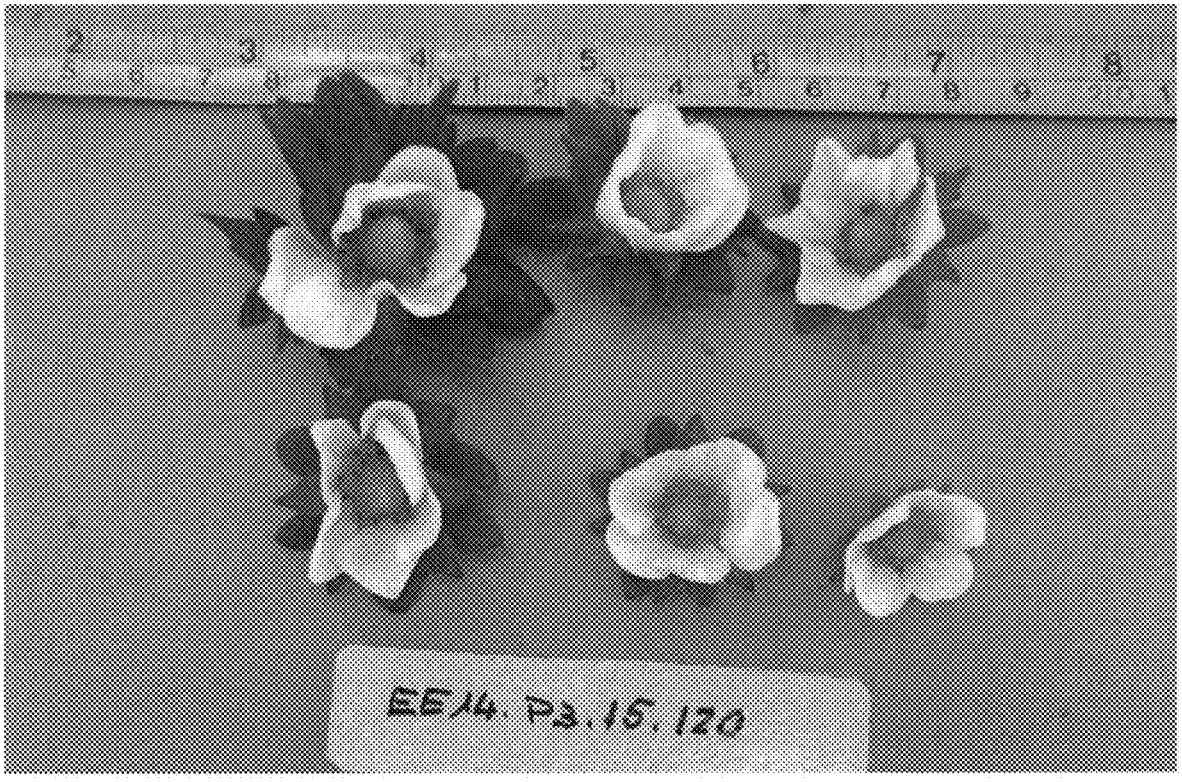

FIG. 9—illustrates specimens of corolla—close view (designate in image as EE14.P3.15.120). Dimensions in centimeters and inches are included.

Figure 10:
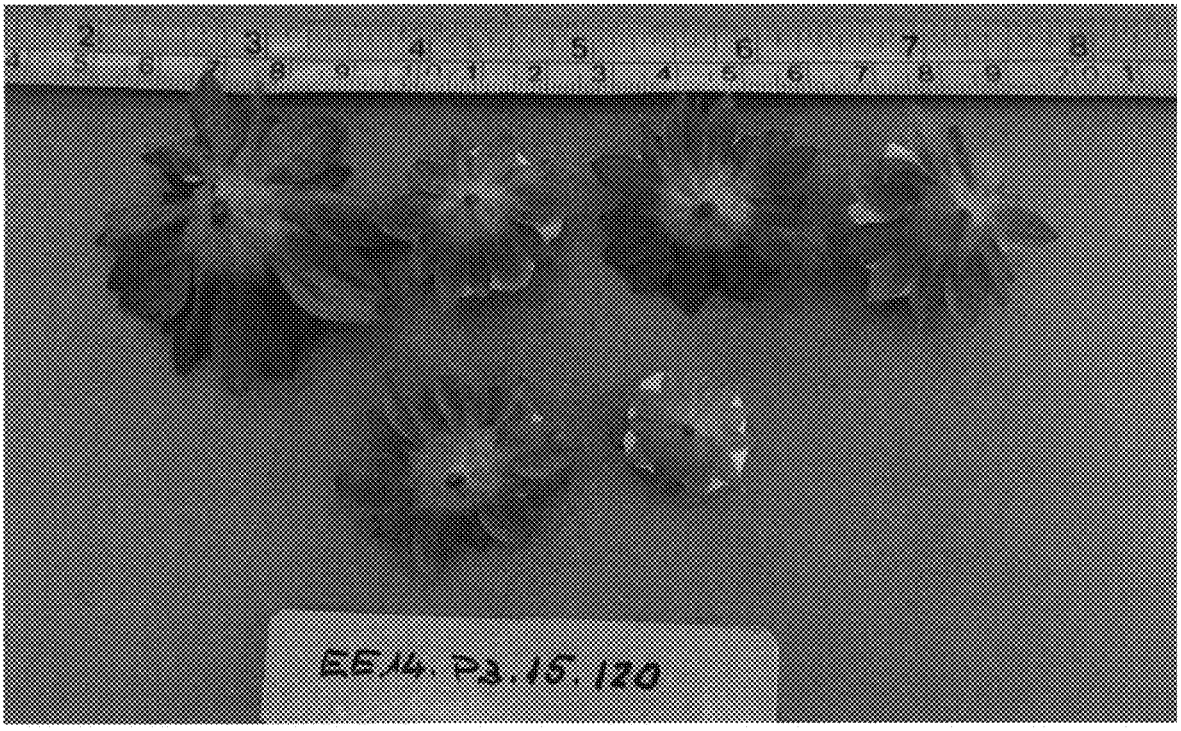

FIG. 10—illustrates specimens of calyx—close view (designate in image as EE14.P3.15.120). Dimensions in centimeters and inches are included.

Figure 11:
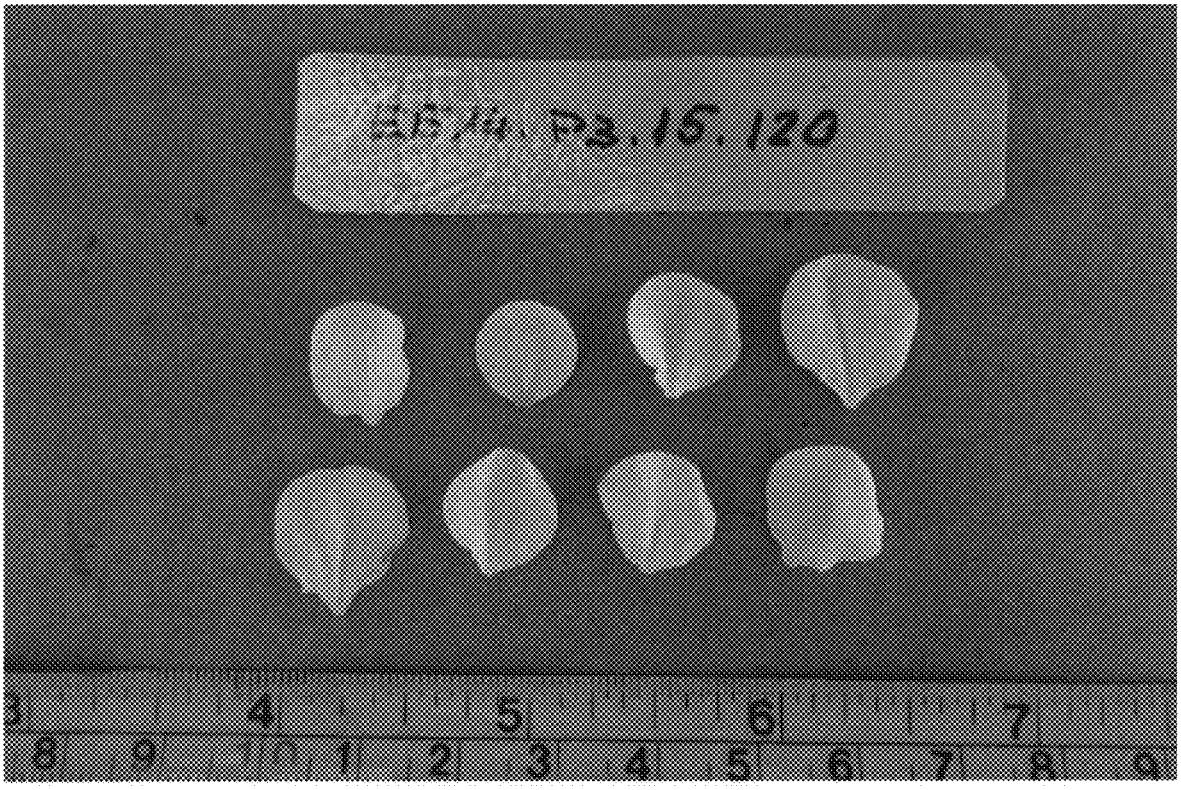

FIG. 11—illustrates specimens of petals of the flowers (designate in image as EE14.P3.15.120). Dimensions in centimeters and inches are included.

Figure 12:
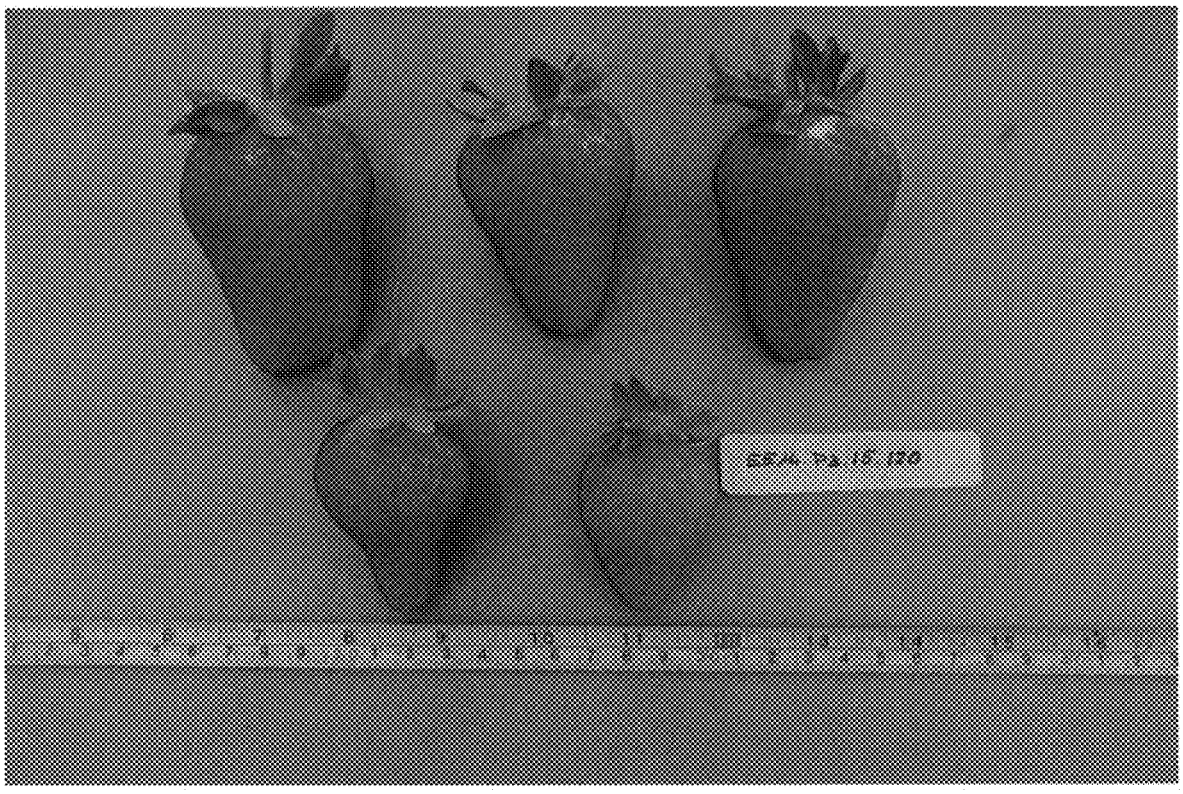

FIG. 12—illustrates specimens of mature fruit—whole (designate in image as EE14.P3.15.120). Dimensions in centimeters and inches are included.

Figure 13:
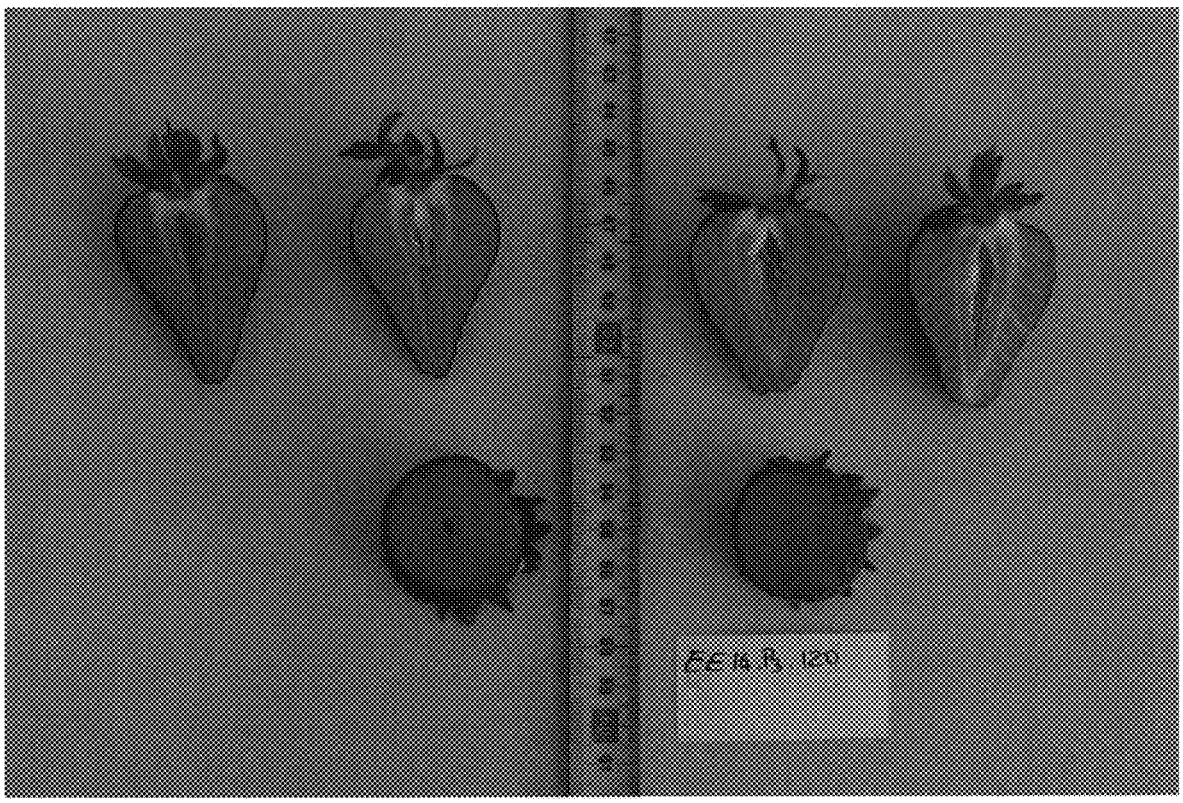

FIG. 13—illustrates specimens of mature fruit—internal sections (designate in image as EE14.P3.15.120). Dimensions in centimeters and inches are included.

Figure 14:
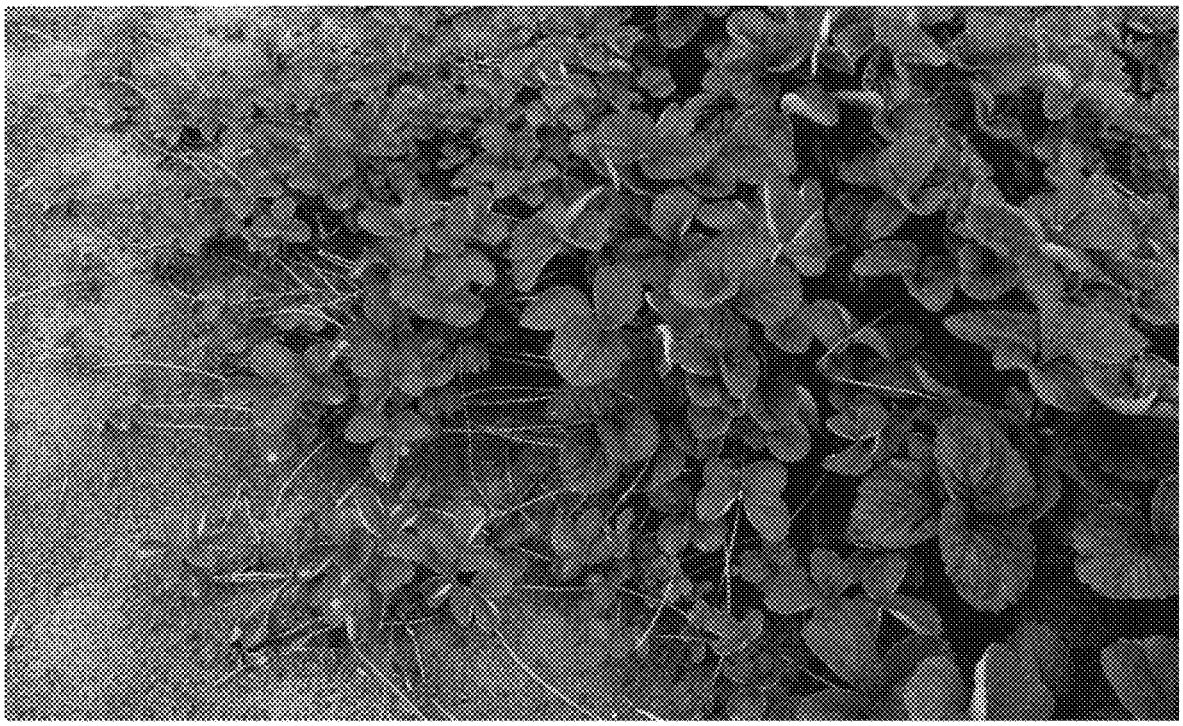

FIG. 14—illustrates specimen of runners (stolons).

Figure 15:
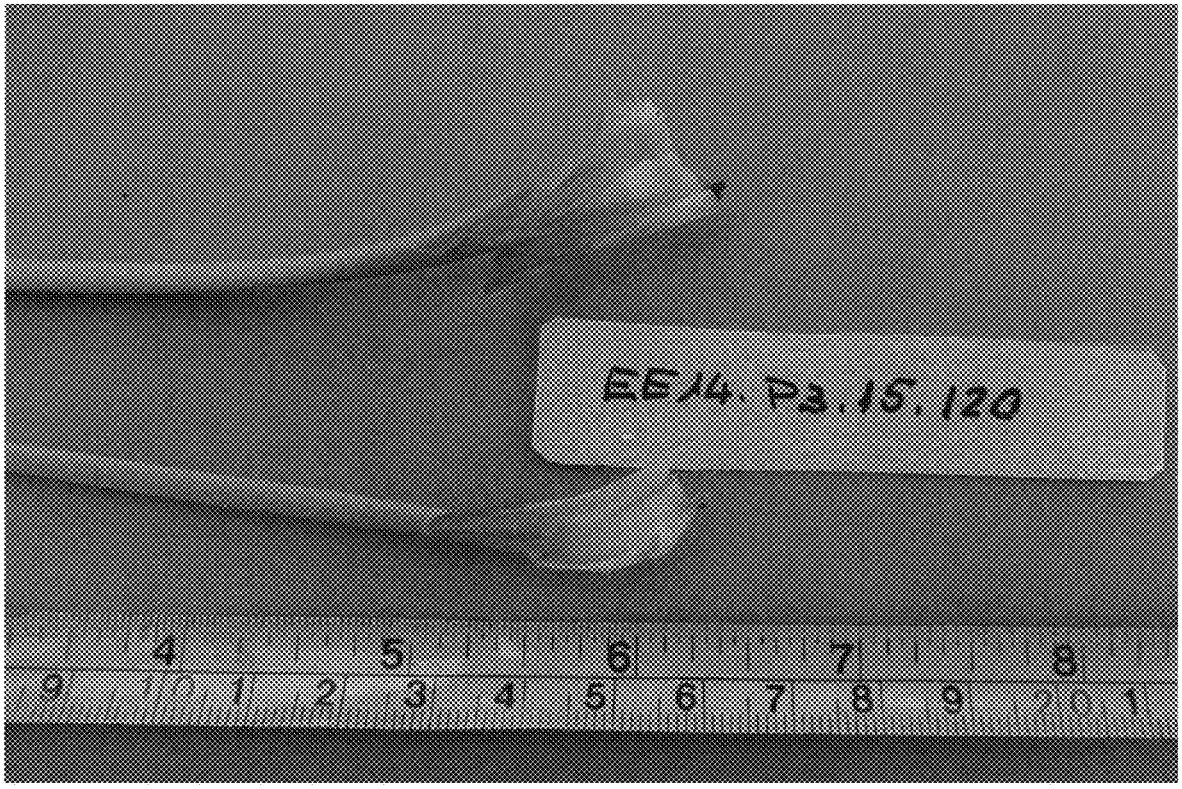

FIG. 15—illustrates specimens of stipule and petiole (designate in image as EE14.P3.15.120). Dimensions in centimeters and inches are included.

DETAILED BOTANICAL DESCRIPTION

The chart used in the identification of colors is that of The Royal Horticultural Society ("R.H.S." Colour Chart), London, England, Edition V. The terminology which precedes reference to the chart has been added to indicate the corresponding color in more common terms. The detailed botanical description is based on plants which were reproduced asexually by the use of stolons at Zielona Gora-Ochla, Poland (located at 51° 848 N-15° 447 E), transplanted at Nova Siri (MT), Italy (located at 40° 08' 40" N -16° 39' 40"

E and 10 meters above sea level) in October and growing under the cover of plastic tunnels.

With regard to stolons, their description took place in Poland. These stolons are derived from frigo plants transplanted in Poland at Zielona Gora Ochla in April. Therefore the age of the plants on which the botanical description was made is between two and eight months from the transplants.

Plant:

*Type*.—Short-day.

*Configuration*.—Semi-upright and semi-dense.

*Vigor*.—Medium to weak.

*Leaf*.—Approximately 16 cm to 19 cm in size.

*Leaflets*.—Number: commonly 3. — size: medium-to large in size, approximately 10.5 cm in length on average, and approximately 8 cm in width on average. — terminal leaflet: commonly moderately longer in length than width, possesses a generally concave cross-section, possesses a crenate margin, and an acute base. — blistering: commonly is weak in quantity. — glossiness on the upper surface: weak. — color: variegated coloration commonly is absent; upper surface coloration commonly being near Green Group N141A to Green Group N141B; and under surface commonly being near Green Group 138C to Green Group 138D. — texture (upper surface): wrinkled with small translucent waxy points and a low presence of trichomes on the whole surface. — texture (lower surface): generally wrinkled with trichomes present, especially on the ribs. — venation pattern: the main transverse ribs are grafted forming an acute angle, at the insertion level of the main transverse rib there is no curvature in the initial part.

*Stolons*.—High in quantity, medium pubescence in density, color is commonly near Yellow-Green Group 145B to Yellow-Green Group 145C, weak or absent anthocyanin coloration, and the distance between plants rooted in the same stolon is approximately 27 cm to 40 cm on average.

*Petioles*.—Approximately 17 cm to 25 cm in length on average, the average minor axis and the average major axis, measured at approximately 3 cm from the base of the stipule are approximately 2.7 mm and 3.5 mm, respectively, and color is commonly near Yellow-Green Group N144C, and commonly bear generally horizontally disposed fine pubescence.

*Stipules*.—Approximately 2.5 cm to 3 cm in length on average, average width of closed stipules is approximately 11 mm, average width of open stipules is approximately 19.5 mm, color is Yellow-Green 145 B while some commonly bear weak anthocyanin coloration of near Red-Purple Group 61C to Red-Purple Group 61D.

*Floral fragrance*.—Slightly present.

Inflorescence:

*Flowering time*.—Very early, second/third week of December in Nova Siri (MT), Italy at 10 meters above sea level.

*Flower disposition*.—Generally above the foliage.

*Flower number*.—Medium, commonly 4 to 6; typically one flower at the beginning of the season.

*Pedicel hairs*.—Pubescence generally disposed somewhat upwards.

*Pedicel color*.—Commonly near Yellow-Green Group 144C.

*Pedicel length*.—The average length of the main and secondary pedicles measured from the base of the calyx, with the first fruit already ripe on the main axis is approximately 18 cm.

*Pedicel diameter*.—The diameter measured at approximately 3 cm from the calyx is approximately 2.6 mm.

*Flower size*.—Large, with primary flowers approximately 2.5 cm to 3.5 cm in diameter on average, and secondary flowers approximately 2.1 cm to 2.6 cm in diameter on average, commonly the open calyx is larger than the diameter than the corolla being approximately 2.6 cm to 4.5 cm in diameter on average.

*Petals*.—Number: approximately 5 to 7 on average, typically — arrangement and shape: overlapping, somewhat rounded overall in configuration with the relationship of the length to the width being substantially equal, and acute apex. — size: approximately 10 mm on average in length and width on average. — color: commonly near White Group NN155A on the upper surface. — texture (upper surface): spongy texture, smooth, glabrous surface, with small translucent points; roughness at the level of insertion on the calyx. — texture (lower surface): evident general roughness, glabrous surface.

*Stamens*.—Average number: approximately 25. — average length: approximately 2 mm to 5 mm. — filament color: Yellow-Green Group 1D.

*Anthers*.—Number is approximately 21 to 25 on average, commonly disposed below the stamen, and color is commonly Yellow Group 12A.

*Pollen*.—In abundance.

*Stigma*.—Shape: very jagged fan shape. — size: an average opening of approximately 400 μm. — texture: Dry waxed stigma, not feathery.

*Style*.—Average length: approximately between 1600 μm-1800 μm. — average diameter: approximately 200 μm, which thins and curves at the level of the insertion on the ovary, entirely crossed by a stylus channel with an average diameter of approximately 38 μm. — shape: Gynobasic style.

*Ovary*.—Superior, with oval shape and average major axis and the average minor axis of approximately 700 μm and 500 μm.

*Sepals*.—Shape: generally lanceolate in configuration; attitude is commonly upwards, and generally extend beyond the petals. — number: approximately 12 to 14 on average. — size: approximately 1.2 cm to 1.6 cm in length on average, and approximately 5 mm to 7 mm in width on average at the broadest point. — color: the upper surface is commonly near Green Group 143A to Green Group 143B and the under surface is commonly near Green Group 141C to Green Group 142B. — texture (upper surface): smooth with trichomes mainly at the margin and translucent waxy points at the basal part. — texture (lower surface): slightly wrinkled with tricomes mainly present on the basal part.

Fruit:

*Bearing*.—Non-remontant.

*Timing*.—Early fruiting commonly with approximately 28 to 34 days from first blooming to first fruit ripening.

*Shape*.—Conical, slightly rhomboid, longer than broad, commonly with a medium difference between terminal and the other fruits.

*Size*.—Large, with the primary fruit approximately 5.0 cm to 6.5 cm in length on average; approximately 4 cm to 4.5 cm in width on average at the broadest point; and approximately 23.4 grams on average.

*Surface*.—Slightly uneven texture with strong glossiness.

*External color*.—Substantially uniform commonly near Red Group 43A to Red Group 43B.

*Internal color*.—Flesh is commonly near Orange-Red Group 33A to Orange-Red Group 33B, and the core is commonly near Orange-Red Group 33A to Orange-Red Group 33B.

*Firmness*.—Good firmness.

*Cavity*.—Small to medium fruit cavity, as illustrated in FIG. 13.

*Achenes*.—Located generally below the fruit surface and cover nearly the entire fruit surface commonly with only a very narrow band (if any) where achenes are absent, and commonly going from near Orange Group 28A to Red Group 43B in coloration, depending of fruit maturity.

*Calyx*.—Commonly slightly raised at the point of attachment, the calyx commonly attaches to the fruit with medium to hard adherence, the sepals are disposed generally slightly upwards, calyx typically extends beyond the overlapping petals when open, and the fruit diameter of calyx in relation to diameter of fruit commonly are slightly bigger.

*Peduncle*.—Long, elliptical shape, approximately 30 cm to 36 cm in length on average for primary fruit, average minor axis and the average major axis measured at approximately 3 cm from the base in cross section are approximately 3.6 mm and 3.8 mm, respectively, and color is commonly near Yellow-Green Group N144C.

*Pedicel*.—Commonly with pubescence extending upwards, and color is commonly near Yellow-Green Group N144C.

*Storability*.—Medium to high.

Development:

*Fertilization*.—Self-fertile.

*Resistance to disease*.—During the time of observations and to date, no sensitivities to any disease were observed.

*Winter hardiness/color tolerance*.—Unknown.

*Drought/heat tolerance*.—Good.

Plants of the 'NSG 120' variety have not been observed under all possible environmental conditions to date. Accordingly, it is possible that the phenotypic expression may vary somewhat with changes in light intensity and duration, cultural practices, and other environmental conditions.

SUPPLEMENTAL COMPARATIVE DATA

Hereafter, additional comparative fruit data is provided for the new variety, the 'NSG 1117' variety, the 'MELISSA' variety (i.e., the male parent) and the 'CHARLENE' variety (i.e., the female variety). The plants were asexually reproduced by the use of stolons in 2017 at Zielona Gora-Ochla, Poland located at 51° 848 N-15° 447 E, and planted in field on Oct. 15, 2017. All varieties were grown under the cover of plastic tunnels at Nova Siri (MT), Italy located at 40° 08' 40" N-16° 39' 40" E (10 meters above sea level). The first pick of the fruit occurred on January 8 and the last pick of the fruit occurred on May 30. The fruit were evaluated and compared on the dates indicated. Average data is as follow:

TABLE 1

Accumulated Production of First Quality Fruit (g/plant)

| variety | February 30th | March 30th | April 30th | May 20th |
|---|---|---|---|---|
| 'NSG 120' | 58 | 234 | 435 | 643 |
| 'NSG 1117' | 24 | 195 | 405 | 600 |

Datos Nicola + 15% + 30%

TABLE 2

Overall Comparison of Average Fruit Weight in Nova Siri-Italy on year 2018

| plant | g/fruit |
|---|---|
| 'NSG 120' | 23.4 |
| 'MELISSA' | 26.0 |
| 'CHARLENE' | 22.0 |
| 'NSG 1117' | 26.2 |

TABLE 3

Average Fruit Weight on Specified Dates on 2018

| variety | March 30th (grams) | April 30th (grams) | May 20th (grams) |
|---|---|---|---|
| 'NSG 120' | 24 | 23,5 | 23 |
| 'MELISSA' | 27 | 26 | 22 |
| 'CHARLENE' | 24 | 22 | 19 |
| 'NSG 1117' | 28 | 24 | 25 |

TABLE 4

Fruit Analysis on May 30,2018

| | 'NSG 120' | 'NSG 1117' | 'CHARLENE' | 'MELISSA' |
|---|---|---|---|---|
| Firmness (average)* | 0.70 | 0.77 | 0.74 | 0.75 |
| Dry Matter (%)** | 9.14 | 8.25 | 8.50 | 8.25 |
| pH (to 202) | 3.40 | 3.60 | 3.80 | 3.93 |
| Acidity as Anhydride Citric (%) | 0.71 | 0.69 | 0.70 | 0.60 |
| Soluble Solids (% Brix) | 8.50 | 7.60 | 8.80 | 9.00 |
| Maturity Index*** | 9.93 | 11.01 | 12.57 | 15.00 |

*Resistance to penetration measured in kilograms using a Turoni (Italy) pentrometer (20 Kg × 0.01).
**Weight of residue from the titration of the fruit after drying at 103° C. until is achieved a constant weight.
***Relation between soluble solids and acidity anhydride.

I claim:

1. A new and distinct strawberry plant characterized by the following combination of characteristics:

(a) exhibits a semi-dense, semi-upright growth habit, (b) displays, on an early basis, white inflorescence at a level generally above the foliage, (c) commonly displays a calyx that is larger than the diameter of the corolla when open, and, (d) forms in abundance attractive early-ripening large, medium red primarily conical fruit having firm flesh that is longer than broad in configuration;

substantially as herein shown and described.

* * * * *